United States Patent
Kim et al.

(10) Patent No.: US 10,368,809 B2
(45) Date of Patent: Aug. 6, 2019

(54) METHOD AND APPARATUS FOR TRACKING A POSITION OF A TUMOR

(71) Applicant: Samsung Electronics Co., Ltd., Suwon-si (KR)

(72) Inventors: Jung-bae Kim, Hwaseong-si (KR); Young-kyoo Hwang, Seoul (KR); Do-kyoon Kim, Seongnam-si (KR); Won-chul Bang, Seongnam-si (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 1081 days.

(21) Appl. No.: 13/930,042

(22) Filed: Jun. 28, 2013

(65) Prior Publication Data
US 2014/0046172 A1    Feb. 13, 2014

(30) Foreign Application Priority Data
Aug. 8, 2012    (KR) ................. 10-2012-0086936

(51) Int. Cl.
*A61B 5/00*    (2006.01)
*A61B 6/00*    (2006.01)
(Continued)

(52) U.S. Cl.
CPC ............ *A61B 5/7275* (2013.01); *A61B 8/085* (2013.01); *A61N 7/02* (2013.01); *G06T 7/251* (2017.01); *G06T 7/277* (2017.01); *A61B 5/0035* (2013.01); *A61B 5/055* (2013.01); *A61B 6/5247* (2013.01); *A61B 8/5261* (2013.01); *A61B 2017/00699* (2013.01); *A61B 2090/364* (2016.02); *A61B 2090/374* (2016.02); *A61B 2090/3762* (2016.02); *G06T 2207/10081* (2013.01); *G06T 2207/10088* (2013.01);
(Continued)

(58) Field of Classification Search
CPC .. G06F 17/50; G06F 17/5004; G06F 17/5018; G06F 17/5095
USPC ......................................................... 703/11
See application file for complete search history.

(56) References Cited

U.S. PATENT DOCUMENTS

| | | | |
|---|---|---|---|
| 4,899,393 A | 2/1990 | Morishita et al. | |
| 8,111,892 B2 | 2/2012 | Hyun et al. | |

(Continued)

FOREIGN PATENT DOCUMENTS

| | | |
|---|---|---|
| KR | 10-0305419 B1 | 1/2000 |
| KR | 10-2007-0095788 A | 10/2007 |

(Continued)

OTHER PUBLICATIONS

Preiswerk, Frank, et al. "A Bayesian framework for estimating respiratory liver motion from sparse measurements." International MICCAI Workshop on Computational and Clinical Challenges in Abdominal Imaging. Springer, Berlin, Heidelberg, 2011.*

(Continued)

*Primary Examiner* — Carolyn A Pehlke
(74) *Attorney, Agent, or Firm* — Cha & Reiter, LLC

(57) ABSTRACT

Provided is a method and apparatus for tracking a tumor position, which changes by the movement of a body. According to various aspects, a location of a tumor position of a target organ may be estimated using images of one or more surrounding organs.

15 Claims, 7 Drawing Sheets

(51) Int. Cl.
- *A61B 8/08* (2006.01)
- *A61N 7/02* (2006.01)
- *A61B 17/00* (2006.01)
- *A61B 5/055* (2006.01)
- *A61B 90/00* (2016.01)
- *G06T 7/246* (2017.01)
- *G06T 7/277* (2017.01)

(52) U.S. Cl.
CPC ............ *G06T 2207/20072* (2013.01); *G06T 2207/20124* (2013.01); *G06T 2207/30096* (2013.01); *G06T 2207/30101* (2013.01)

(56) References Cited

U.S. PATENT DOCUMENTS

| | | | | |
|---|---|---|---|---|
| 2006/0074292 | A1* | 4/2006 | Thomson | A61B 6/032 600/411 |
| 2007/0041639 | A1* | 2/2007 | Von Berg | G06T 7/0012 382/173 |
| 2007/0276214 | A1* | 11/2007 | Dachille | G06T 7/0012 600/407 |
| 2008/0123927 | A1* | 5/2008 | Miga | A61B 19/52 382/131 |
| 2009/0088897 | A1* | 4/2009 | Zhao | A61B 19/2203 700/250 |
| 2010/0289813 | A1 | 11/2010 | Nobe et al. | |
| 2011/0028844 | A1 | 2/2011 | Hyun et al. | |
| 2011/0103666 | A1 | 5/2011 | Ohishi | |
| 2011/0135177 | A1 | 6/2011 | Ohishi | |
| 2011/0150312 | A1* | 6/2011 | Takanami | G06T 17/20 382/131 |
| 2012/0014559 | A1* | 1/2012 | Suehling | G06K 9/6207 382/103 |
| 2012/0027261 | A1 | 2/2012 | Frank et al. | |
| 2012/0035462 | A1* | 2/2012 | Maurer, Jr. | A61B 6/5247 600/411 |
| 2012/0046545 | A1 | 2/2012 | Averbuch | |
| 2012/0051664 | A1* | 3/2012 | Gopalakrishnan | G06T 11/005 382/294 |
| 2012/0071757 | A1 | 3/2012 | Salcudean et al. | |
| 2012/0082351 | A1 | 4/2012 | Higgins et al. | |
| 2012/0250966 | A1* | 10/2012 | Fujisawa | G06T 7/0016 382/131 |
| 2012/0253170 | A1 | 10/2012 | Kim et al. | |

FOREIGN PATENT DOCUMENTS

| | | |
|---|---|---|
| KR | 10-2008-0032612 A | 4/2008 |
| KR | 10-2009-0098842 A | 9/2009 |
| KR | 10-2009-0127091 A | 12/2009 |
| KR | 10-0979335 B1 | 1/2010 |
| KR | 10-1132536 B1 | 6/2010 |
| KR | 10-1028365 B1 | 8/2010 |
| KR | 10-2010-0126262 A | 12/2010 |
| KR | 10-1017610 B1 | 2/2011 |
| KR | 10-1144579 B1 | 2/2011 |
| KR | 10-1047615 B1 | 5/2011 |
| KR | 10-2011-0078274 A | 7/2011 |
| KR | 10-1118549 B1 | 12/2011 |

OTHER PUBLICATIONS

Brock, Kristy K., et al. "Feasibility of a novel deformable image registration technique to facilitate classification, targeting, and monitoring of tumor and normal tissue." International Journal of Radiation Oncology Biology Physics 64.4 (2006): 1245-1254.*

Dagon, Benoit, Charles Baur, and Vincent Bettschart. "A framework for intraoperative update of 3D deformable models in liver surgery." Engineering in Medicine and Biology Society, 2008. EMBS 2008. 30th Annual International Conference of the IEEE. IEEE, 2008.*

Preiswerk, Frank, Patrik Arnold, Beat Fasel, and Philippe C. Cattin. "Robust tumour tracking from 2D imaging using a population-based statistical motion model." In Mathematical Methods in Biomedical Image Analysis (MMBIA), 2012 IEEE Workshop on, pp. 209-214. IEEE, 2012.*

* cited by examiner

METHOD AND APPARATUS FOR TRACKING A POSITION OF A TUMOR

CROSS-REFERENCE TO RELATED APPLICATIONS

This application claims the benefit under 35 USC § 119(a) of Korean Patent Application No. 10-2012-0086936, filed on Aug. 8, 2012, in the Korean Intellectual Property Office, the entire disclosure of which is incorporated herein by reference for all purposes.

BACKGROUND

1. Field

The following description relates to methods and apparatuses for tracking the position of a tumor using estimation.

2. Description of Related Art

Due to recent developments in medical science, focal treatments for tumors have progressed from invasive surgery such as an abdominal operation to minimal-invasive surgery. Some examples of non-invasive surgeries may be performed using a gamma knife, a cyber knife, a high-intensity focused ultrasound (HIFU) knife, and the like. In particular, the recently commercialized HIFU knife is being widely used as an eco-friendly treatment.

HIFU treatment is a surgical method that may remove or treat tumors by concentrating high-intensity focused ultrasounds onto a tumor area, which leads to focal destruction or necrosis of the tumor's tissue. Typically, a diagnostic medical image accurately showing the position of a tumor site is required to precisely concentrate HIFU on the tumor site. The medical images may be acquired using image diagnosis technology, such as ultrasound, computed tomography (CT), and magnetic resonance imaging (MRI), and the like, are used for HIFU treatment.

However, medical images may not precisely display a location of a tumor inside a patient's body, in real-time, due to the movement of the patient, for example, due to the breathing of the patient. As a result, a tumor site shown on a medical image may not be completely accurate.

SUMMARY

A method of tracking a tumor position, the method including generating a target organ model and a surrounding organ model based on a medical image comprising anatomical information of a target organ having a tumor and a surrounding organ located on a periphery of the target organ, updating the surrounding organ model based on a real-time image of the target organ and the surrounding organ, updating the target organ model based on the updated surrounding organ model, and estimating a position of the tumor included in the target organ based on the updated target organ model.

The updating of the target organ model may comprise estimating a position and shape of the target organ.

The updating of the target organ model may comprise extracting characteristics of the target organ from the real-time image, and estimating a position and a shape of the target organ based on the extracted characteristics of the target organ.

The updating of the target organ model may comprise estimating a position and shape of the target organ based on the extracted characteristics of the target organ and the updated surrounding organ model.

The updating of the target organ model may comprise estimating a position and shape of the target organ based on the extracted characteristics of the target organ and a respiratory phase of a target body.

The generating of the target organ model and the surrounding organ model may comprise generating models showing shapes of the target organ and the surrounding organ, and modeling movement of the generated models.

The generating of the target organ model and the surrounding organ model may comprise modeling positions and shapes of the target organ and the surrounding organ based on a respiratory phase of a target body.

The target organ model and the surrounding organ model may be generated before the real-time image is input.

A non-transitory computer-readable storage medium may have stored thereon a program that when executed by a computer performs the method described herein.

In an aspect, there is provided an apparatus for tracking a tumor position, the apparatus including an organ model generating unit configured to generate a target organ model and a surrounding organ model based on a medical image comprising anatomical information of a target organ having a tumor and a surrounding organ located on a periphery of the target organ, a surrounding organ model registering unit configured to update the surrounding organ model based on a real-time image of the target organ and the surrounding organ, a target organ model registering unit configured to update the target organ model based on the updated surrounding organ model, and a tumor estimating unit configured to estimate a position of the tumor included in the target organ based on the updated target organ model.

The target organ model registering unit may be configured to estimate a position and a shape of the target organ based on the updated surrounding organ model.

The target organ model registering unit may be configured to extract characteristics of the target organ from the real-time image and estimate a position and a shape of the target organ based on the extracted characteristics of the target organ.

The target organ model registering unit may be configured to estimate the position and the shape of the target organ based on the extracted characteristics of the target organ and the updated surrounding organ model.

The target organ model registering unit may be configured to estimate a shape and a change of the target organ model based on extracted characteristics of the target organ and respiration of a target body.

The target organ model generating unit may be configured to generate models showing shapes of the target organ and surrounding organ, and model movement of the generated models.

The target organ model generating unit may be configured to model positions and shapes of the target organ and surrounding organ based on a respiratory phase of a target body.

The target organ model and the surrounding organ model may be generated before the real-time image is input.

In an aspect, there is provided an imaging device including a surrounding organ imager configured to determine characteristics of one or more surrounding organs that surround a target organ, based on image characteristics of the one or more surrounding organs, and a target organ imager configured to estimate a shape and a size of the target organ based on the determined characteristics of the one or more surrounding organs.

The imaging device may further comprise a tumor estimator configured to estimate a location of a tumor on the target organ based on the estimated shape and size of the target organ.

The surrounding organ imager may be configured to receive a higher resolution image of the one or more surrounding organs, and to modify the higher resolution image using a lower resolution image of the one or more surrounding organs that is received in real-time.

The higher resolution image may comprise one of a computed tomography (CT) image and a magnetic resonance (MR) image, and the lower resolution image may comprise an ultrasound image.

The target organ imager may be configured to estimate the shape and the size of the target organ based on a respiratory phase of a patient which includes the target organ.

Other features and aspects may be apparent from the following detailed description, the drawings, and the claims.

Figure 1:
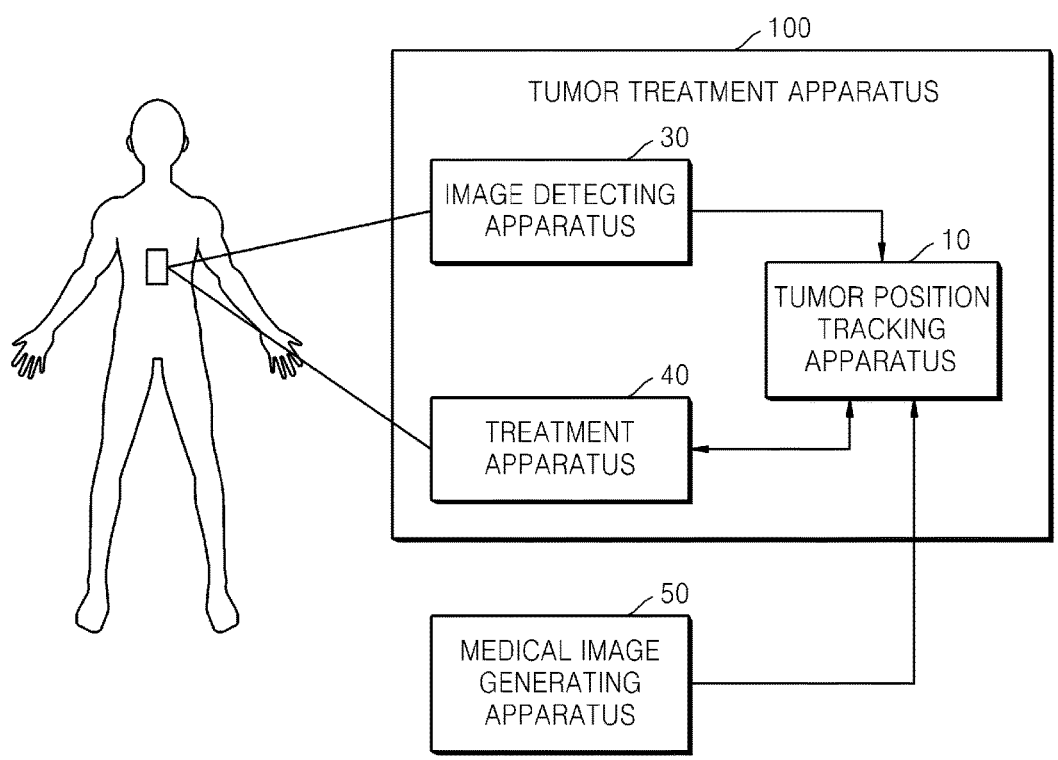
FIG. 1 is a diagram illustrating an example of a tumor treatment system.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

FIG. 1 illustrates an example of a tumor treatment system. Referring to FIG. 1, the tumor treatment system includes a tumor treatment apparatus 100 and a medical image generating apparatus 50. In this example, the tumor treatment apparatus 100 includes an image detecting apparatus 30, a treatment apparatus 40, and a tumor position tracking apparatus 10.

The tumor treatment apparatus 100 may remove a tumor by tracking the position of the tumor within a patient. Therefore, even if the position of the tumor changes due to activity of the target patient, the tumor treatment apparatus 100 may continuously track the position of the tumor to thereby remove the tumor.

For example, the tumor treatment apparatus 100 may acquire a real-time image of an organ that has position changes due to activity of the patient based on models of organs. The tumor treatment apparatus 100 may track in real time the position of the tumor within the organ using the acquired real-time image of the organ.

The tumor treatment apparatus 100 may track the position of a tumor even if the tumor within the target organ may not be identified from the real-time image using surrounding organ models of surrounding organs and a target organ model of the target organ. For example, the tumor treatment apparatus 100 may match the surrounding organ models with the real-time image to determine the position and shape of the surrounding organs. In addition, the position and shape of the target organ may be determined based on the determined position and shape of the surrounding organs. In this example, the tumor treatment apparatus 100 may track the position of the tumor within the target organ according to the determined position and shape of the target organ.

The image detecting apparatus 30 may detect an image of the target body in real-time by transmitting ultrasound waves to the target body and receiving the reflected ultrasound waves. Because the image detecting apparatus 30 may detect the image of the target body in real-time, image changes according to the movement of the target body may be included in the image. For example, organs in the human body may move or change their shape due to breathing. Accordingly, the image detecting apparatus 30 may output the real-time image of the target body that shows the movement or changes of the organ in real-time to the tumor tracking unit 10.

The image detecting apparatus 30 may generate image data, for example, using responses that occur when a source signal created from a probe installed therein is delivered to a specific portion of the target body for diagnosis by practitioners such as doctors. For example, the source signal may include various signals such as ultrasonic waves and X-rays. An example of an ultrasonography machine which detects a three-dimensional image from a patient's body using ultrasonic waves is described herein as an example of the image detecting apparatus 30.

A probe of the ultrasonography machine is generally made of a piezoelectric transducer. For example, when an ultrasonic wave in the range of 2-18 MHz is delivered from the probe of the image detecting apparatus 30 toward a specific portion inside the patient's body, this ultrasonic wave may be partially reflected from layers among various different tissues. For example, the ultrasonic wave may especially be reflected in regions where the density changes in the target body, such as blood cells within blood plasma and small structures within organs. The reflected ultrasonic wave causes the piezoelectric transducer of the probe to vibrate, and the piezoelectric transducer may output electrical pulses depending on the vibrations. These electrical pulses may be converted into an image.

The image detecting apparatus 30 may output various images such as a 2-dimensional image, a three-dimensional (3D) image, and the like. The image detecting apparatus may output three-dimensional images through the following method. While changing the location and orientation of the probe with respect to a specific portion on the target body, a plurality of cross-sectional images for the specific portion of the target body may be detected. Next, the image detecting apparatus 30 accumulates the cross-sectional images and generates image data of three-dimensional volume which three-dimensionally indicates the specific portion of the patient's target body. In this example, the method of generating the image data of three-dimensional volume by accumulating the cross-sectional images is called a multi-planar reconstruction (MPR) method. However, images which are obtainable by the image detecting apparatus 30, for example, ultrasound images, may be acquired in real-time, but it may be difficult to accurately identify internal structures of organs or tumors from the ultrasound images.

The medical image generating apparatus 50 is an apparatus for generating medical images of the target body. For example, the medical image generating apparatus 50 may generate a computed tomography (CT) or magnetic resonance (MR) image. That is, the medical image generating apparatus 50 may generate images that allow contours and internal structures of organs or tumors to be more clearly identified. The CT image or MR image is advantageous in that positions of organs or tumors are clearly identified. However, a CT image or a MR image is disadvantageous in that it is difficult to acquire real-time images showing the changes of the positions or the changes of the organs due to the movement or breathing of patients. Furthermore, the CT image is acquired by capturing images using radiation and thus there is a possibility of patients being subject to prolonged exposure to radiation. Therefore, the image capturing should be desirably performed in a short time. Furthermore, acquiring the MR image is a slow process, and it is thus difficult to obtain real-time images from the CT and MR images.

According to various aspects, the tumor treatment apparatus 100 may acquire images in real-time from the image detecting apparatus 30, may generate organ models using the medical images acquired from the medical image generating apparatus 50, and may estimate moved positions or changed shapes of organs by matching or registering the real-time images with the organ models, thereby tracking the position of a tumor within the organ.

The treatment apparatus 40 is an apparatus that may be used to remove or treat tumors. For example, the treatment apparatus 40 may be a high-intensity focused ultrasound (HIFU) apparatus. The HIFU apparatus may treat or remove tumors by focusing ultrasonic waves on a region to be treated, and irradiating the tumor region with the ultrasonic waves to result in the focal destruction or necrosis of the tumors. When HIFU apparatus 40 continuously concentrates the focus of high-intensity focused ultrasound on the specific region, the temperature of cells subjected to irradiation increases, and tissues that increase in temperature above a certain level go under necrosis.

Figure 2:
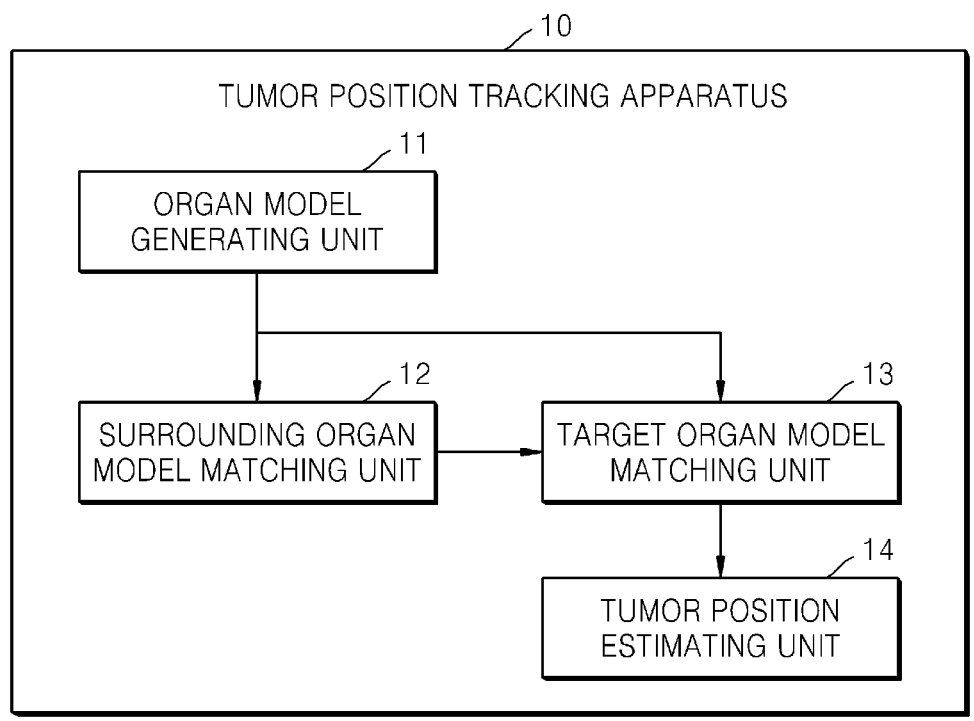
FIG. 2 is a diagram illustrating an example of the tumor position tracking apparatus 10 shown in FIG. 1.

FIG. 2 illustrates an example of the tumor position tracking apparatus 10 shown in FIG. 1. Referring to FIG. 2, the tumor position tracking apparatus 10 includes an organ model generating unit 11, a surrounding organ model matching unit 12, a target organ model matching unit 13, and a tumor position estimating unit 14. The tumor position tracking apparatus 10 may track the position of a tumor based on image information that is input from the medical image generating apparatus 50 and image detecting apparatus 30.

The organ model generating unit 11 may receive medical images from the medical image generating apparatus 50 to generate organ models which include shapes and characteristics of organs. According to various aspects, the organ model may include a target organ model and a surrounding organ model. The target organ model may be an organ model including tumors, and the surrounding organ model is an organ model adjacent to the target organ model. The organ model generating unit 11 may output the generated organ models to the surrounding organ model matching unit 12 and/or target organ model matching unit 13. The organ model generating unit 11 may output the generated surrounding organ model to the surrounding organ model matching unit 12, and output the generated target organ model to the target organ model matching unit 13.

The surrounding organ model matching unit 12 may determine the position and shape of the surrounding organ model by matching or registering the surrounding organ model and the real-time images. For example, the surrounding organ model matching unit 12 may update the position and shape of the surrounding organ model based on characteristics extracted from the surrounding organ model and the real-time images. The real-time image is an image that is input from the image detecting apparatus 30 and may illustrate the target organ and surrounding organs. Characteristics extracted from the surrounding organ model and the real-time images may include the contours of organs, blood vessels, cysts and calcifications. The surrounding organ model matching unit 12 may update the position and shape of the surrounding organ model to ensure that the positions of characteristics extracted from the surrounding organ model and the real-time images are matched with each other, and outputs the updated surrounding organ model to the target organ model matching unit 13.

The target organ model matching unit 13 may determine the position and shape of the target organ model on the basis of the updated surrounding organ model. For example, the target organ model matching unit 13 may determine the position and shape of the target organ model according to the position and shape of the updated surrounding organ model. The target organ model matching unit 13 may receive the target organ model from the organ model generating unit 11.

The target organ model matching unit 13 may match the target organ model and the real-time image on the basis of the real-time image that is input from the image detecting apparatus 30. The target organ model matching unit 13 may update the target organ model by matching anatomical characteristics of a target organ extracted from real-time image and anatomical characteristics of the target organ model. According to various aspects, even if the anatomical characteristics of the target organ extracted from the real-time image are inadequate for performing matching, the target organ model matching unit 13 may update the target organ model based on the updated surrounding organ model. In this example, the target organ model matching unit 13 may determine the position and shape of the target organ model according to the position and shape of the updated surrounding organ model.

The target organ model matching unit 13 may determine the position and shape of the target organ based on all of the anatomical characteristics of the target organ that are extracted from the updated surrounding organ model and the real-time image. As an example, if the target organ is a liver, it may be difficult to extract blood vessels of the liver from the real-time image due to cirrhosis, thus making it difficult to estimate the position and shape of the liver using only the real-time image of the liver. Accordingly, the surrounding organ model matching unit 12 may preferentially determine the positions and shapes of the surrounding organs by extracting characteristics of the surrounding organs located nearby the liver. In this example, the target organ model matching unit 13 may estimate the position and shape of the liver according to the position and shape of the determined surrounding organs, enabling the position and shape of the liver to be estimated even in a situation where it is difficult to extract characteristics of the liver.

The tumor position estimating unit 14 may estimate the position of the tumor in the target organ model. For example, the tumor position estimating unit 14 may acquire the position of the tumor from a target tumor model generated from the organ model generating unit 11 and the medical image that is input from the medical image generating apparatus 50. When the target organ model matching unit 13 updates the target organ model (that is, moves or changes the target organ model), the tumor position estimating unit 14 may estimate which position the tumor moves to in target organ model.

Figure 3:
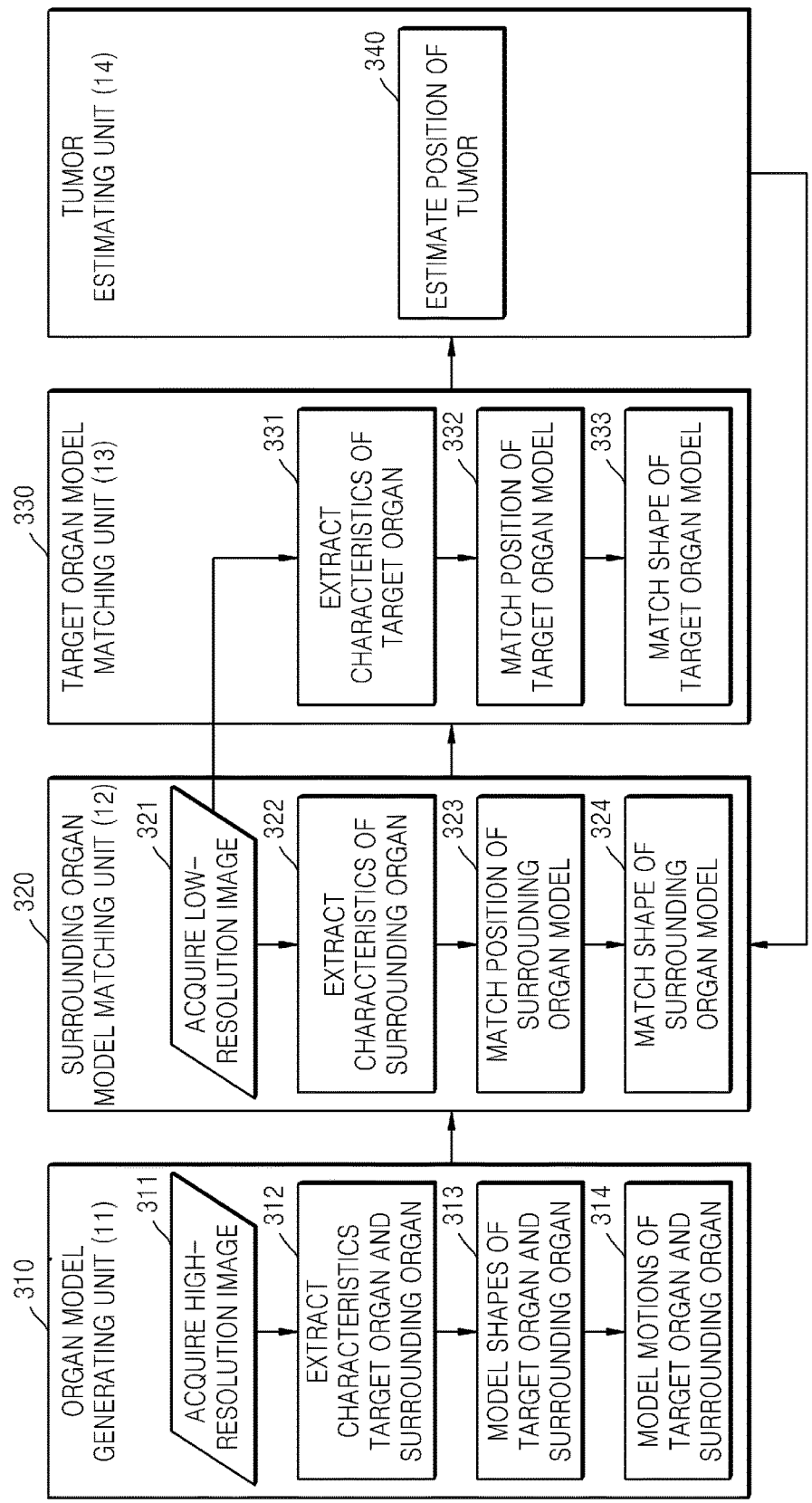
FIG. 3 is a diagram illustrating examples of operations of the tumor position tracking apparatus 10 of FIG. 1.
Figure 4:
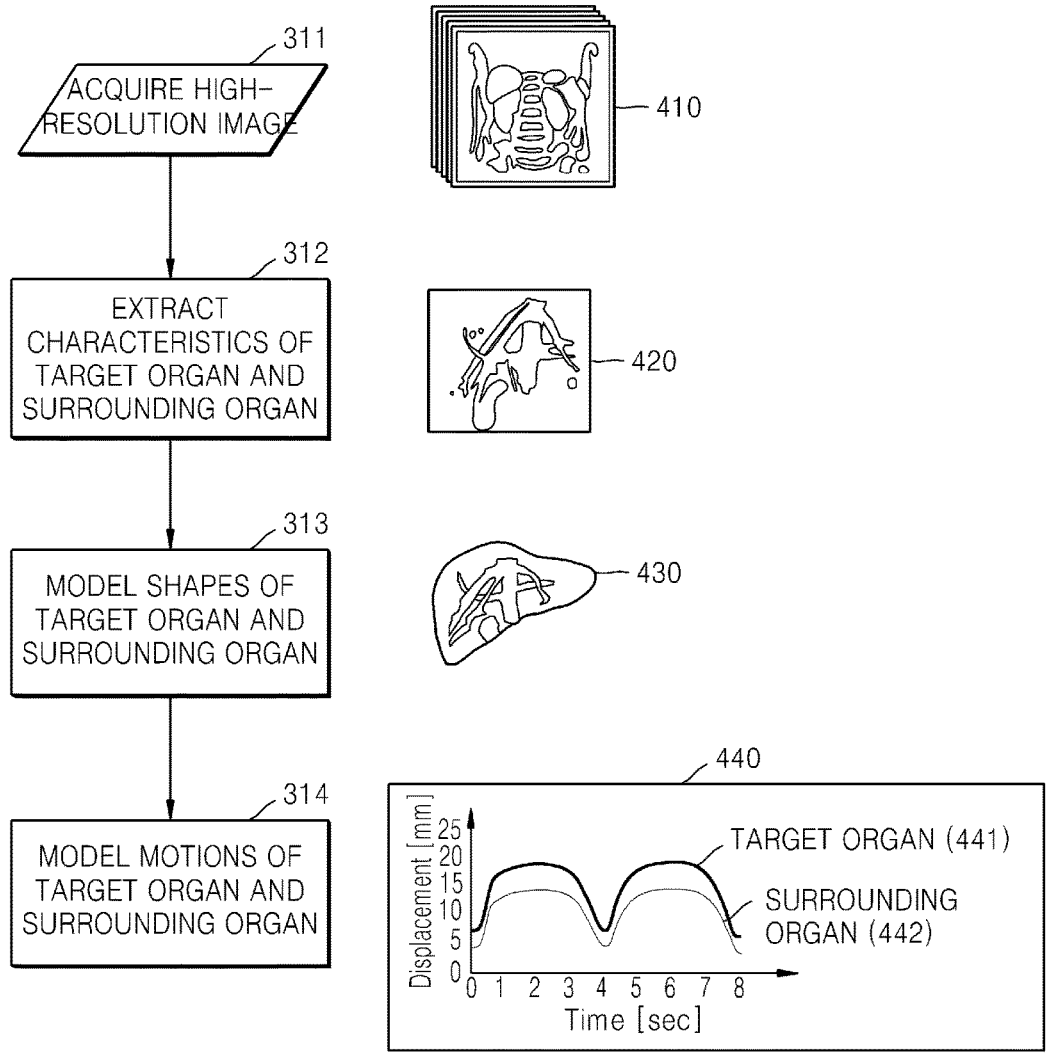
FIG. 4 is a diagram illustrating an example of modeling an organ.
Figure 5:
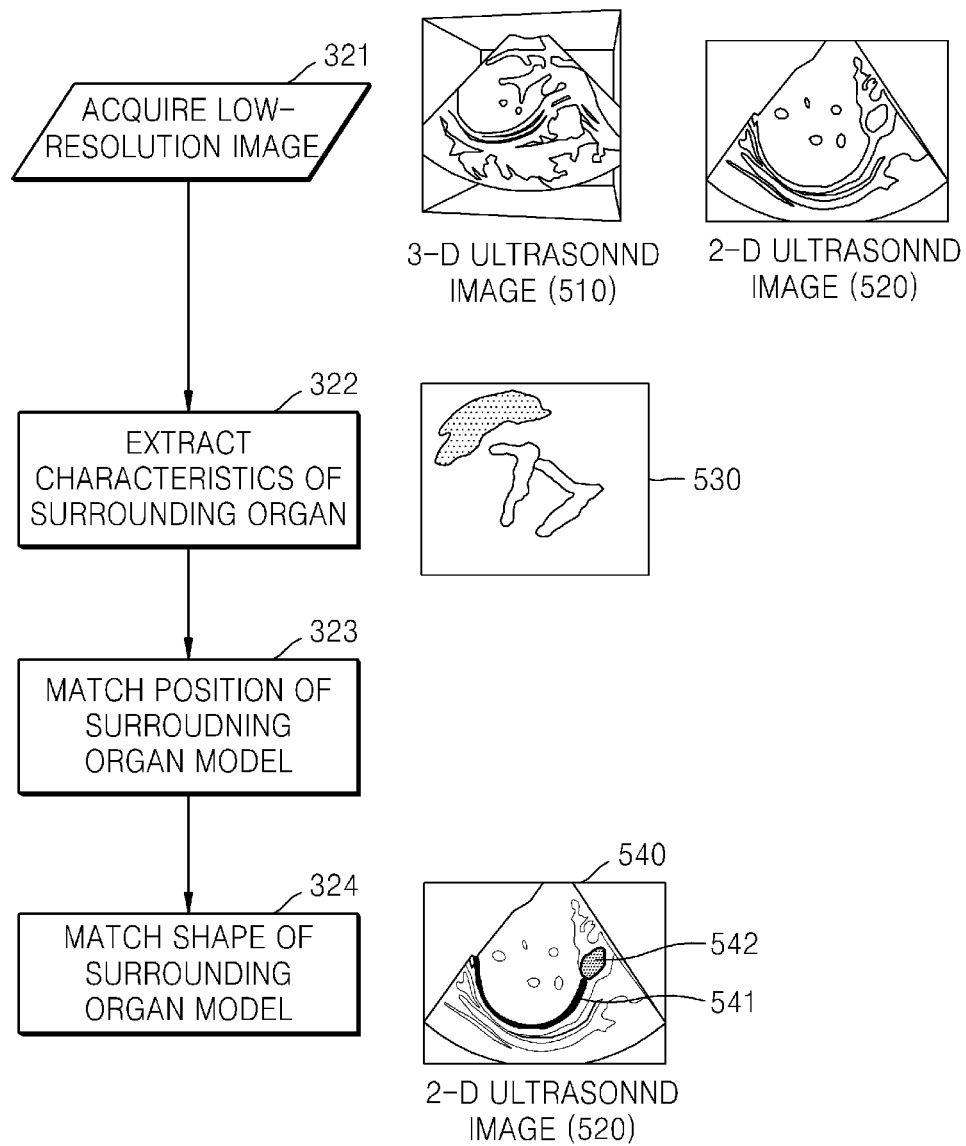
FIG. 5 is a diagram illustrating an example of matching a surrounding organ.
Figure 6:
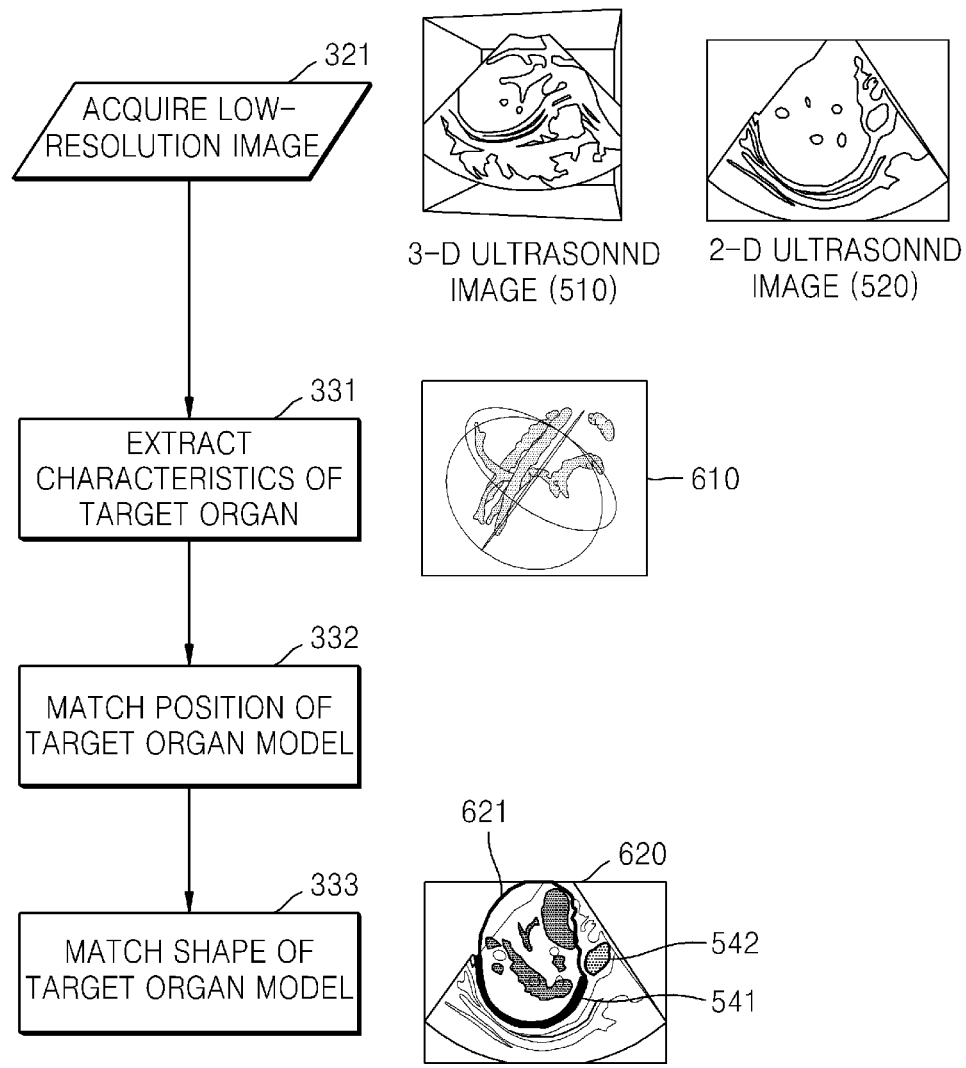
FIG. 6 is a diagram illustrating an example of matching a target organ.

FIG. 3 illustrates examples of operations of the tumor position tracking apparatus 10 in FIG. 1. Examples of the operation of FIG. 3 are shown in FIGS. 4 to 6. Accordingly, FIGS. 3 to 6 are described together hereafter.

Referring to FIG. 3, in 310, the organ model generating unit 11 acquires a high-resolution image and generates a target organ model and a surrounding organ model. In 311, the organ model generating unit 11 acquires the high-resolution image. For example, the high-resolution image may be an image enabling blood vessels or tumors included in organs to be identified. As an example, the high-resolution image may be an MR image or CT image. For example, the organ model generating unit 11 may receive the CT or MR images depending on a breathing period. Therefore, the organ model generating unit 11 may generate models for organs depending on the breathing period. For example, as illustrated in FIG. 4, the organ model generating unit 11 may acquire a high-resolution image 410. The high-resolution image 410 of FIG. 4 is an example of images showing the target organ and surrounding organs.

In 312, the organ model generating unit 11 extracts characteristics of the target organ and the surrounding organs from the acquired high-resolution image. For example, the organ model generating unit 11 may extract anatomical characteristics of organs such as volume, contour or blood vessels of the organs which are included in high-resolution image. In the operation of extracting the volume of an organ, 3D graph cut, which is a region growing method, may be used from foreground and background images, and a Gaussian mixture model may be used in the operation of extracting blood vessels. The organ model generating unit 11 may use 3-D active shape model (ASM) algorithm in generating a 3-D organ model. Image 420 in FIG. 4 is an example of an image showing anatomical characteristics extracted from the high-resolution image 410.

In 313, the organ generating unit 11 models the shapes of the target organ and the surrounding organ. The organ model generating unit 11 may generate a graphical model using the anatomical characteristics of the organs extracted in operation 312. For example, organ model generating unit 11 may use a method of acquiring a 3D mesh using a marching cubes algorithm with respect to surfaces of each split volume. Model 430 in FIG. 4 is an example of the organ model generated on the basis of the extracted anatomical characteristics.

In 314, the organ model generating unit 11 models movements of the target organ and the surrounding organs. Modeling of the movements may include an operation of modeling changes in position of each organ according to breathing, and an operation of modeling changes of each organ's shape according to breathing.

The graph 440 in FIG. 4 illustrates modeling of movement of the target organ and the surrounding organs. The X axis of the graph 440 represents time, and the Y axis represents displacement. In this example, the graph 440 shows a displacement of an organ according to breathing. A curve 441 shows a displacement of the target organ, and a curve 442 shows a displacement of the surrounding organ. The graph 440 illustrates an example in which the displacement of the target organ is greater than the displacement of the surrounding organ. The organ model generating unit 11 may model the motions of the organs based on the displacement of organs according to breathing, as illustrated in the graph 440. Hence, a graphical model may illustrate time-dependent changes of the positions and shapes of the organs which occur due to interactions between the organs. The movement of the organ due to breathing may include a passive movement of the surrounding organs including lungs, depending on the active movement of the rib cage and diaphragm. For example, organs moving spontaneously according to the movement of diaphragm may be a liver, kidney, pancreas, inferior vena cava, gall bladder, and the like.

In 320, the surrounding organ model matching unit 12 acquires a low-resolution image and matches the surrounding organ model and the low-resolution image. In 321, the surrounding organ model matching unit 12 acquires the low-resolution image. For example, the low-resolution image may have a lower resolution than that of the high-resolution image acquired in operation 311. For example, the low-resolution image may be a three-dimensional or two-dimensional ultrasound image. It is possible to obtain the ultrasound images in real-time. For example, the surrounding organ model matching unit 12 may acquire the low-resolution image in real-time during breathing. A 3-dimensional ultrasound image 510 and a 2-dimensional ultrasound image 520 in FIG. 5 are examples of the low-resolution image. In this example, an ultrasound image has lower resolution than MR or CT images, but is capable of being acquired in real-time.

In 322, the surrounding organ model matching unit 12 extracts characteristics of the surrounding organs. For example, contours of organs may be extracted. Also, the surrounding organ model matching unit 12 may extract unique anatomical characteristics of each organ. For example, the anatomical characteristics of a kidney are renal cortex, renal medulla or renal sinus. An image 530 in FIG. 5 is an image showing characteristics of the surrounding organs extracted from the three-dimensional ultrasound image 510 or two-dimensional ultrasound image 520.

In 323, the surrounding organ model matching unit 12 matches the position of the surrounding organ model. For example, the surrounding organ model matching unit 12 may determine the size, direction and position of the surrounding organ model based on the extracted anatomical characteristic of each organ.

In 324, the surrounding organ model matching unit 12 matches the shape of the surrounding organ model. The surrounding organ model matching unit 12 may match real-time images that are input by changing the shape of the surrounding organ model.

An image 540 of FIG. 5 illustrates an example in which the surrounding organ model matching unit 12 matches a diaphragm 541 and a gall bladder 542. For example, if the target organ is a liver and surrounding organs of the liver are the diaphragm and the gall bladder, the surrounding organ model matching unit 12 may determine the positions and shapes of the diaphragm model 541 and the gall bladder model 542.

In 330, the target organ model matching unit 13 may match the target organ model based on the surrounding organ model. The surrounding organ model that is input to the target organ model matching unit 13 may be a model matched through operation 320. For example, the surrounding organ model that is input to the target organ model matching unit 13 may be a model in which positions and shapes are updated by matching the surrounding organ model as constructed on the basis of a high-resolution image, with a low-resolution image. Therefore, the matched (or updated) surrounding organ model may illustrate positions and shapes of the surrounding organs which are changed according to the breathing of a target body.

In 331, the target organ model matching unit 13 extracts characteristics of the target organ. For example, the target organ model matching unit 13 may extract anatomical characteristics of the target organ to be treated, from the low-resolution image acquired in operation 321. An image 610 in FIG. 6 is an example of an image showing characteristics of the target organ extracted from the target organ.

In 332, the target organ model matching unit 13 matches the position of the target organ model. Based on a respiratory phase of a target body, for example, the target organ model matching unit 13 may determine a position where the target organ model will be placed. The respiratory phase of the target body may be determined according to the position of the updated surrounding organ model. The target organ model matching unit 13 may determine the respiratory phase of the target body, and determine the position of the target organ using the movement modeling result of the target organ modeled in operation 314. Also, the target organ model matching unit 13 may perform rigid matching on the low-resolution image by moving or rotating the target organ model.

In 333, the target organ model matching unit 13 may match the shape of the target organ model. The target organ model matching unit 13 may change the shape of the target organ model by estimating the shape of the target organ and may estimate changes in shape of the target organ model based on the determined respiratory phase and characteristics extracted from the target organ. The target organ model matching unit 13 may perform non-rigid matching on the estimated target organ model and the low-resolution image.

In 340, the tumor position estimating unit 14 estimates the position of the tumor located within the target organ. For example, the tumor position estimating unit 14 may receive the matched target organ model as updated from the target organ model matching unit 13, and estimate the position of the tumor located within the target organ model. An image 620 in FIG. 6 illustrates an example of the target organ model matching unit 13 matching the position and shape of the target organ. The target organ model matching unit 13 matches the position and shape of liver model 621 based on a diaphragm model 541 and a gall bladder model 542.

Figure 7:
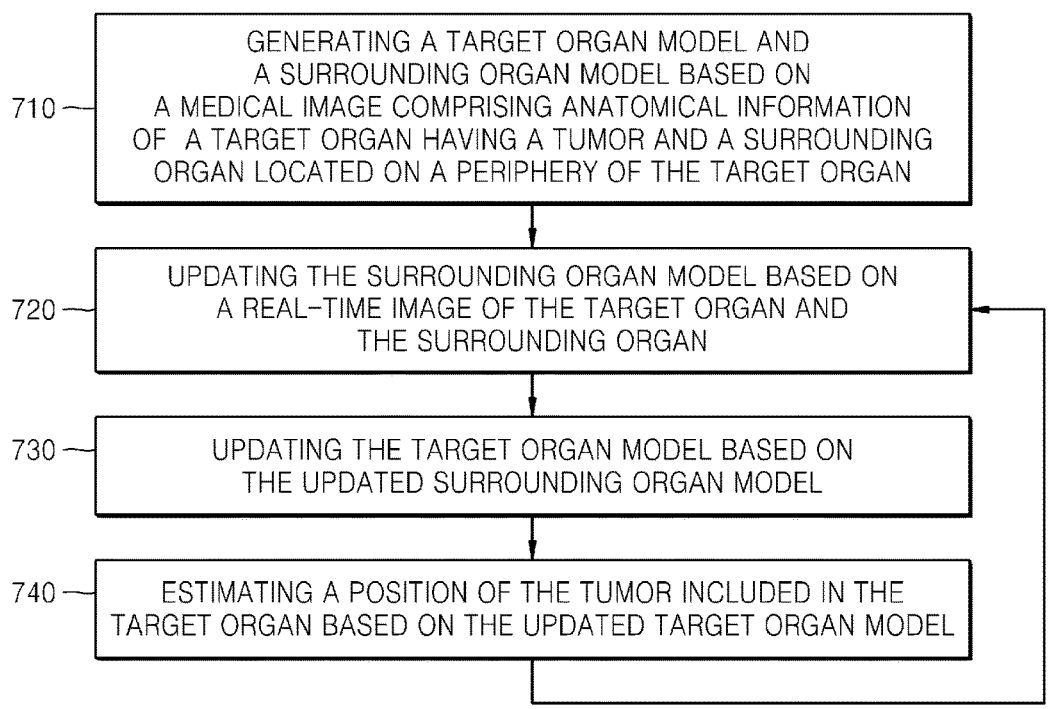
FIG. 7 is a diagram illustrating an example of a tumor position tracking method.

FIG. 7 illustrates an example of a method for tracking positions of tumors. It should be appreciated that the contents mentioned previously in regard to the tumor position tracking apparatus 10 illustrated in FIG. 2 are also applicable to the example of FIG. 7.

In 710, the organ model generating unit 11 generates a target organ model and a surrounding organ model using a medical image that includes anatomical information of a target organ having a tumor and organs surrounding the target organ. For example, the target organ model and the surrounding organ model may be generated before real-time images are input.

In 720, the surrounding organ model matching unit 12 matches real-time images showing the target organ and the surrounding organ with the surrounding organ model.

In 730, the target organ model matching unit 13 matches the target organ model based on matched surrounding organ model.

In 740, the tumor position estimating unit 14 estimates the position of the tumor based on the matched target organ model. When operation 740 is terminated, each operation may be repeated from operation 720.

According to various aspects, the use of information regarding surrounding organs enables the position of a tumor in the target organ to be tracked by estimating the position and shape of the target organ.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable storage mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of tracking a tumor position, the method comprising:
generating a target organ model of a target organ having the tumor and a surrounding organ model of at least two surrounding organs located at the periphery of the target organ, based on a medical image comprising anatomical information of the target organ having the tumor and the at least two surrounding organs, by extracting unique anatomical characteristics of each organ, the unique anatomical characteristics of each organ comprising unique detailed anatomical structure of each organ;
updating a shape, direction of movement, and a position of the at least two surrounding organs in the surrounding organ model based on the extracted unique anatomical characteristics of each organ and a dynamic image of the target organ and the at least two surrounding organs;

updating the target organ model based on the updated surrounding organ model, wherein the updating of the target organ model comprises:
  determining a respiratory phase of a target body in the dynamic image based on the position of the at least two surrounding organs from the updated surrounding organ model; and
  updating a shape, direction of movement, and a position of the target organ model based on the determined respiratory phase, the extracted unique anatomical characteristics of each organ, and the dynamic image;
estimating a position of the tumor included in the target organ based on the updated target organ model; and
transmitting information regarding the estimated position of the tumor to a treatment apparatus,
wherein the medical image has a first resolution and the dynamic image has a second resolution that is different than the first resolution.

2. The method of claim 1, wherein the updating of the target organ model comprises:
  extracting characteristics of the target organ from the dynamic image; and
  estimating the position and the shape of the target organ based on the extracted characteristics of the target organ.

3. The method of claim 2, wherein the updating of the target organ model comprises estimating the position and shape of the target organ based on the extracted characteristics of the target organ and the updated surrounding organ model.

4. The method of claim 2, wherein the updating of the target organ model comprises estimating the position and shape of the target organ based on the extracted characteristics of the target organ and the respiratory phase of the target body.

5. The method of claim 1, wherein the generating of the target organ model and the surrounding organ model comprises:
  generating models of shapes of the target organ and the at least two surrounding organs; and
  modeling movement of the generated models.

6. The method of claim 1, wherein the generating of the target organ model and the surrounding organ model comprises modeling positions and shapes of the target organ and the at least two surrounding organs based on the respiratory phase of the target body.

7. The method of claim 1, wherein the target organ model and the surrounding organ model are generated before the dynamic image is obtained.

8. A non-transitory computer-readable storage medium having stored thereon a program that when executed by a computer performs the method of claim 1.

9. An apparatus for tracking a tumor position, the apparatus comprising:
  one or more processors configured to:
  generate a target organ model of a target organ having the tumor and a surrounding organ model of at least two surrounding organs located at the periphery of the target organ, based on a medical image comprising anatomical information of the target organ having the tumor and at least two surrounding organs, by extracting unique anatomical characteristics of each organ, the unique anatomical characteristics of each organ comprising unique detailed anatomical structure of each organ;
  update a shape, direction of movement, and a position of the at least two surrounding organs in the surrounding organ model based on the extracted unique anatomical characteristics of each organ and a dynamic image of the target organ and the at least two target organs;
  update the target organ model based on the updated surrounding organ model, wherein to update the target organ model, the one or more processors is configured to:
  determine a respiratory phase of a target body in the dynamic image based on the position of the at least two surrounding organs from the updated surrounding organ model; and
  update a shape, direction of movement, and a position of the target organ model based on the determined respiratory phase, the extracted unique anatomical characteristics of each organ, and the dynamic image;
  estimate a position of the tumor included in the target organ based on the updated target organ model; and
  transmit information regarding the estimated position of the tumor to a treatment apparatus,
  wherein the medical image has a first resolution and the dynamic image has a second resolution that is different than the first resolution.

10. The apparatus of claim 9, wherein, to update the surrounding organ model, the one or more processors is configured to extract characteristics of the target organ from the dynamic image and estimate the position and the shape of the target organ based on the extracted characteristics of the target organ.

11. The apparatus of claim 10, wherein, to update the surrounding organ model, the one or more processors is configured to estimate the position and the shape of the target organ based on the extracted characteristics of the target organ and the updated surrounding organ model.

12. The apparatus of claim 9, wherein, to update the surrounding organ model, the one or more processors is configured to estimate the shape and a change of the target organ model based on the extracted characteristics of the target organ and the respiratory phase of the target body.

13. The apparatus of claim 9, wherein, to generate the target organ model and the surrounding organ model, the one or more processors is configured to generate models of shapes of the target organ and surrounding organ, and model movement of the generated models.

14. The apparatus of claim 9, wherein, to generate the target organ model and the surrounding organ model, the one or more processors is configured to model positions and shapes of the target organ and surrounding organ based on the respiratory phase of the target body.

15. The apparatus of claim 9, wherein the target organ model and the surrounding organ model are generated before the dynamic image is obtained.

* * * * *